United States Patent [19]
Cushman

[11] Patent Number: 5,223,866
[45] Date of Patent: Jun. 29, 1993

[54] SMALL, SIMPLE AND COST-EFFECTIVE SCHEINER-PRINCIPLE OPTOMETER WITH COMPUTER INTERFACE FOR AUTOMATED ASSESSMENT

[75] Inventor: William B. Cushman, Pensacola, Fla.

[73] Assignee: The United States of America as represented by the Secretary of the Navy, Washington, D.C.

[21] Appl. No.: 814,156

[22] Filed: Dec. 30, 1991

[51] Int. Cl.$^5$ .............................. A61B 3/02; A61B 3/10
[52] U.S. Cl. .................... 351/243; 351/211; 351/223; 351/237; 351/239
[58] Field of Search ............... 351/211, 223, 237, 239, 351/243, 203

[56] References Cited
U.S. PATENT DOCUMENTS

| | | | |
|---|---|---|---|
| 4,778,268 | 10/1988 | Randle | 351/237 |
| 4,943,151 | 7/1990 | Cushman | 351/211 |
| 4,997,269 | 3/1991 | Cushman | 351/243 |

OTHER PUBLICATIONS

Helmholtz's Treatise on Physiological Optics (translated) Edited by James P. C. Southall, vol. 1, pp. 124-126 & 133 (1962).

*Primary Examiner*—Rodney B. Bovernick
*Assistant Examiner*—Evelyn A. Lester
*Attorney, Agent, or Firm*—A. David Spevack; William C. Garvert

[57] ABSTRACT

A Scheiner-principle optometer for automated assessment of accommodative state is disclosed. The specific advantages of the instant invention over earlier ones are: a) simplicity of design, b) hand held, portable implementation, c) light weight, d) small size, e) low manufacturing cost, and, f) the use of a monochromatic light source to eliminate the effects of chromatic aberrations in the subject's eye.

9 Claims, 1 Drawing Sheet

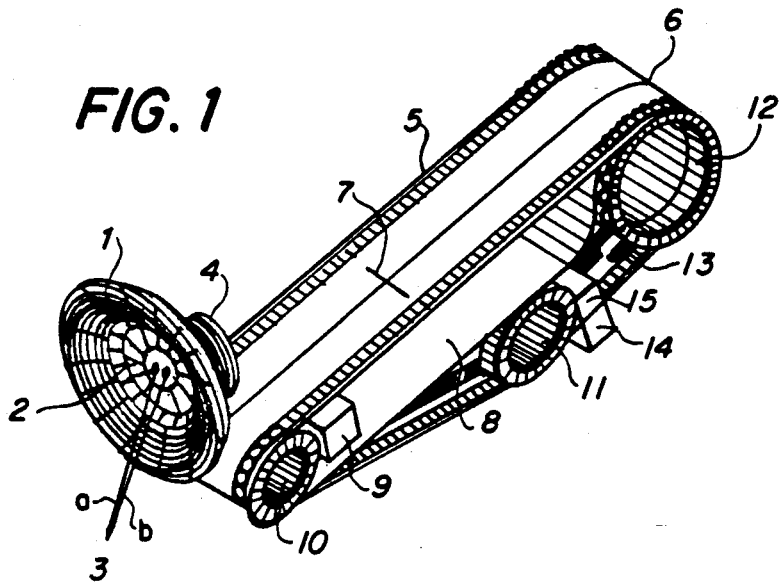
FIG. 1
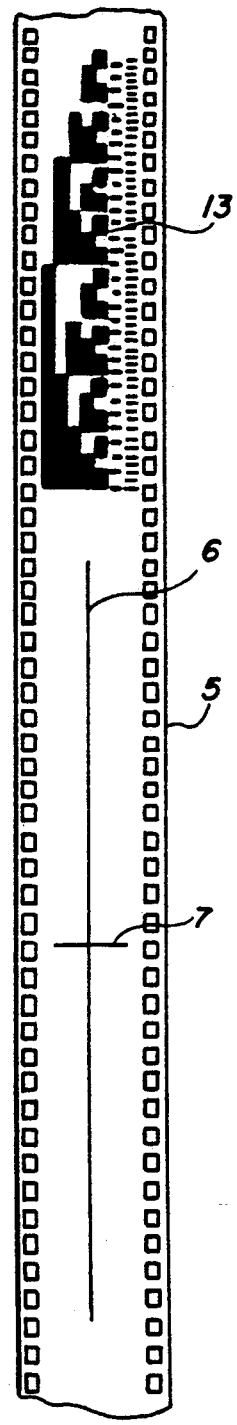
FIG. 2
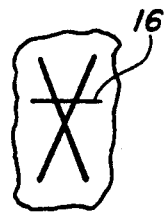
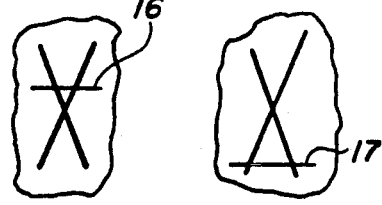
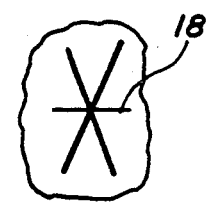
FIG. 3a    FIG. 3b    FIG. 3c

1

SMALL, SIMPLE AND COST-EFFECTIVE SCHEINER-PRINCIPLE OPTOMETER WITH COMPUTER INTERFACE FOR AUTOMATED ASSESSMENT

BACKGROUND OF THE INVENTION

1. Field of the Invention

This invention relates to optometers and particularly to a Scheiner-principle optometer apparatus, and method therefore, for measuring the resting state of accommodation, and for providing recognition of this accommodative state in a machine readable format to ancillary devices, such as to a computer.

2. Description of the Prior Art

This application is an improvement on the related invention of U.S. Pat. No. 4,997,269 entitled "SCHEINER-PRINCIPLE POCKET OPTOMETER FOR SELF EVALUATION AND BIOFEEDBACK ACCOMMODATION TRAINING" both of which have the same inventor and are commonly assigned to the Government of the United States. The need for precise lens accommodation to bring visual targets into sharp focus on the retina is far more urgent at night when contrast is very low, than in bright daylight. Unfortunately, it is at precisely this time that many individuals become myopic and further reduce the quality of an already poor visual image. In many professions this phenomenon, sometimes called the "dark focus of accommodation", is of little consequence. For pilots flying at night, however, it can mean the difference between life and death. A reliable screening instrument capable of measuring the refractive state of individuals in the dark could, therefore, provide useful preventive information. In those situations where feedback to the individual being tested is undesirable, such as when screening potential pilot candidates or making wardroom assessments before night operations, some means must be provided to enable a second party to "read" the optometer. The optometer disclosed herein provides a means to convert the optometer setting into machine readable formats such as a voltage level, or binary coded decimal or straight binary encoding, which could then be input directly to a small computer or remote display device for evaluation.

SUMMARY OF THE INVENTION

Accordingly, an object of this invention is to provide an improved optometer apparatus and method.

Another object of this invention is to provide a Scheiner principle optometer for screening for undesirable conditions such as dark or empty field myopia.

Another object of this invention is to provide a small, hand held, simple, economical, and easily portable optometer for screening for undesirable conditions such as dark or empty field myopia.

A further object of this invention is to provide an improved optometer apparatus, and method therefore, which can be easily interfaced with ancillary equipment such as a computer or remote display device.

These and additional objects of the invention are accomplished by interposing a positive lens between the "string" of a Thomas Young's optometer and the Scheiner-principle apertures that work in conjunction with an automatic reading system to permit automated monitoring of readings.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1 is a detailed view of the essential elements of an exemplary embodiment of the invention showing their relationship relative to one another;

FIG. 2 is a detailed view of the filmstrip used by the apparatus, showing details of the line and crossing line seen by a user, and the position encoding area contained thereon; and FIG. 3a, b and c show three views of the image seen by a user of an exemplary embodiment of the invention during adjustment of the crossing line relative position.

DESCRIPTION OF THE PREFERRED EMBODIMENTS

Before proceeding with the Detailed Description, the terms "optometer," "Scheiner-principle optometer" and "dark focus of accommodation" are defined below to aid in the reader's understanding of the present invention.

Optometer—Any one of several objective or subjective devices for measuring the refractive state of the eye. (Synonyms: opsimeter, optimeter, refractometer)

Scheiner-principle optometer—An optometer employing, as an operating principle, multiple pupillary apertures to produce a corresponding multiplicity of images when the image viewed is not in focus.

Dark focus of accommodation—A phenomenon, generally recognized as the "resting state" of the eye in the absence of sufficient stimulation to activate focusing mechanisms. This situation usually occurs in the dark and, thus, it is called the "dark focus of accommodation." This "resting state" in the dark is typically myopic, so a synonym for the phenomenon is "night myopia." A related phenomenon is called "empty field myopia."

Referring now to the drawings, FIG. 1 shows a preferred embodiment of the invention for measuring the accommodative state of a person by the act of adjusting the relative position of a crossing bar observed subjectively to coincide with the intersection of two lines visible to the subject in accordance with the further teaching of the present invention.

In the preferred embodiment of FIG. 1, a rubber eye guard 1 is shown through which a person looks into a pinhole aperture plate 2. The pinhole aperture plate 2 contains two pinhole apertures 3a & b located horizontally equidistant from the center of the pinhole aperture plate with a distance between aperture centers (not shown) of approximately 3 millimeters. It should, however, be realized that there can be more than two pinhole apertures in the pinhole aperture plate 2, and that they can be disposed in a vertical or horizontal alignment or in any other desired alignment near the center of the pinhole aperture plate 2. Also, where there are more than two pinhole apertures in the plate 2, they can be aligned in any other suitable geometric configuration near or about the center of the plate 2.

A positive Badal lens 4 is placed proximal to the pinhole aperture plate 2 such that the optical axis of the Badal lens 4 is coincident with the center of the pinhole aperture plate. Filmstrip 5 which is a movable extended image source, is placed adjacent to the lower edge of the Badal lens at the filmstrip's lower end and inclined away from the Badal lens such that the center of the filmstrip's viewing area is located on the optical axis of the Badal lens at a distance of one focal length of the Badal lens, and the upper end of the filmstrip's viewing area is at a height above the optical axis of the Badal lens equal to the distance below the optical axis of the Badal lens of the lower end of the filmstrip's viewing area. In the preferred embodiment of the instant invention disclosed herein the filmstrip is comprised of a photographic negative with marking line 6 running the long axis of the filmstrip and crossing marking line 7 perpendicular to the long axis of the film. The markings are transparent to facilitate back lighting as will become clear below.

A person using this optometer adjusts the optometer such that the intersection of an apparent "x" formed optically by dual images of the line passing through the two pinhole apertures, 3, and the crossing line are in coincidence. When this coincidence is achieved, then the distance that the crossing line is from the focal distance of the Badal lens represents that person's dioptric deviation from focusing at infinity. This distance may be converted to diopters using the following relationship:

$$Sd = B^2 M - B$$

where Sd is the person's dioptric deviation in diopters, B is the power of the Badal lens in diopters and M is the distance between the Badal lens and the crossing line in meters. The distances so derived are for the optical axis of the Badal lens and must be trigonometrically expanded to account for the incline of the scale relative to the optical axis. Solving the equation gives the lens power required to correct a subjects eye to infinity. That is, negative numbers indicate myopia, and positive numbers indicate hyperopia.

The preferred embodiment of FIG. 1 has provision for back-illumination of the line 6 and crossing line 7 using diffusing reflector 8 and light emitting diode array 9. It is desirable that the light emitting diodes be of a narrow-bandwidth type emitting principally at about 585 nanometers wavelength (yellow light) to minimize chromatic aberrations within the eye. A commercially available example of the light emitting diode is the HLMP 3850 manufactured by the Hewlett-Packard Corporation and by other manufacturers. While a light source 9 of monochromatic yellow light is preferred, it should be noted that a light source of any other wavelength or combination of wavelengths of visible light could be used for the back illumination of the line and the crossing line.

The filmstrip 5 forms a continuous loop supported by idle rollers 10 and 11 and driving roller 12. The driving roller also contains a means for the person using the device to turn it, such as a knob, and bearings, all not shown in the interest of clarity.

In the preferred embodiment of the instant invention the filmstrip 5 also contains an encoded area, 13 which can be used to convert the relative position of the filmstrip loop on the driving and idle rollers into a machine readable format. As shown in the figures, and more notably FIG. 2, this is a binary encoded format with 7 bits of resolution which can be read by photodetectors, 14, from the light either passed or blocked by the encoded area from light emitting array, 15. It is desirable that, in this case, the light emitting array be emitting in the infrared end of the spectrum to avoid optical interference with the rest of the optometer. It should be clear to those skilled in the art that this approach to position encoding is by no means the only one available, and it is not my purpose to so indicate. A viable alternative, for example, would be to place an absolute encoding optical "potentiometer", or even a simple potentiometer within the above mentioned driving roller, 12.

The apparatus shown in FIG. 1 may be contained within a structure and provided with power supply and data connections by means apparent to those of ordinary skill in the art.

FIG. 2 shows a detailed view of the filmstrip, as it might appear when unrolled from it's continuous loop form and flattened. In FIG. 2, 5 indicates the filmstrip in it's entirety, 6 indicates the line along the long axis of the filmstrip, 7 indicates the crossing line, and 13 indicates the encoded area.

FIG. 3 shows three views a, b, c of the image that may be seen by a user of the optometer disclosed herein. In FIG. 3a, 16 indicates a condition where the crossing line is viewed above the intersection formed by the line, 6, as it passes through the apertures, 3, to form an apparent "X", indicating that the optometer should be adjusted to bring the crossing line downward. In FIG. 3b, 17 indicates a condition where the crossing line is viewed below the intersection formed by the line, 6, as it passes through the apertures, 3, to form an apparent "X", indicating that the optometer should be adjusted to bring the crossing line upward. In FIG. 3c, 18 indicates a condition where the crossing line is viewed coincident with the intersection formed by the line, 6, as it passes through the apertures, 3 a & b, to form an apparent "X", indicating that the optometer is adjusted properly. The images shown in FIG. 3 assume an orientation of the optometer disclosed herein as depicted in FIG. 1. That is, with the end of the line closest the subject at the bottom of the instrument as it is held.

When a person views the optometer of FIG. 1 and is, for example, myopic, there is a specific point on the line, 6, that is closer to the Badal lens 4 than one focal distance of the Badal lens, and that emits light which exits from the apertures 3 as two bundles of light with the right amount of divergence to exactly cancel the excess convergence in the eye that is myopic. As a result, the two bundles of light from the apertures 3 (and that originated from a specific point on the line, 6) are brought to coincidence on the retina of the person's eye. All other points on the line 6 will emit light bundles through the apertures 3 that either converge or diverge too much to be coincident on the retina of the person's eye. Therefore, light from these other points on the line 6 will paint a double image on the retina which, since they are vertically displaced as explained before, will appear to the person's eye as two lines that intersect at the point of coincidence, as shown in FIG. 3a, b, & c.

A similar explanation can be made for the conditions of emmetropia and hyperopia, with the point of coincidence only being changed with the different conditions. In the case of the exemplary embodiment of FIG. 1, with the pinhole apertures 3 located horizontally, displacements of the image of the line 6 and crossing line 7 will also be horizontal. The crossing line 7 is itself oriented horizontally, so a multiple image will overlap and continue to appear as one line, albeit a longer one.

The exit apertures 3a & b are small, thus causing the blur circles of images of points or markings on the line 6 and crossing line 7 to also be small and to appear to be in focus at a plurality of focal distances. Since the image being viewed by the person's eye appears to be in focus there is no stimulus for accommodation. The lack of an accommodative stimulus effectively opens an accommodative control feedback loop, thus facilitating the measurement of the phenomenon of dark focus of accommodation without actually being in total darkness.

Therefore, what has been described is a Scheiner-principle optometer apparatus, and method therefore, for measuring the resting state of accommodation, and for providing recognition of this accommodative state in a machine readable format to ancillary devices, such as to a computer or auxiliary display. The apparatus is based on Scheiner's (Scheiner, *Oculus* p 32-49 1619. Referenced in: von Helmholtz, H. *Handbook of physiological optics* (ed.) J. C. Southall, Dover Publishers, Inc., New York, Volume 1, pp 124-126, 1962) practice of dividing an image into a plurality of images with the use of multiple small apertures placed close to the eye, and Thomas Young's (Young, Thomas, (1801) *Phil. Transact.* P.I. p. 34. Referenced in: von Helmholtz, H. *Handbook of physiological optics* (ed.) J. C. Southall, Dover Publishers, Inc., New York, Volume 1, p 133, 1962) elaboration of this practice by placing a fine string on a dark bar extending from close to the eye to a distance encompassing the range of accommodation of interest. The multiple apertures, usually two, divide the image into a number of images equal to the number of apertures, that remain essentially in focus due to the long depth of field afforded by small apertures. If, however, the subject's eye is accommodated at a distance that coincides with the distance of the object being viewed, then the images overlap on the retina and only one is discerned. In Thomas Young's application of this principle, the image of a fine string on a dark bar is brought to coincidence at the point of accommodation, but diverges beyond and before that point. This effect presents an "X" on the retina, with the crossing point of the "X" being the point on the string at the exact distance of accommodation. Thomas Young's device is elegant in concept, but limited in range to the length of dark bar and string used. Obviously, accommodative distances beyond infinity are impossible with this device, and accommodative distances even approaching infinity are limited by structural constraints.

The difficulty in range of accommodation afforded by Thomas Young's optometer is overcome in the instant invention disclosed herein by placing a positive lens, such as the Badal lens 4, between the "string" of Thomas Young's optometer and the Scheiner-principle apertures, such as 3 a & b. A positive lens so placed has a focal distance physically closer than infinity, thus allowing the entire apparatus to be considerably shortened and also extending the measurement range of the apparatus to beyond infinity if the focal distance of the lens is less than the physical length of the apparatus. In the preferred embodiment of the instant invention disclosed herein a 20 diopter lens is used as lens 4, giving a focal distance of 5 centimeters, and an effective dioptric divergence (from the perspective of the subject) of 4 diopters/centimeter away from the focal distance of the lens. A line 6 is used in the preferred embodiment of the instant invention disclosed herein, in a manner similar to that of Thomas Young's, except that the center of the line 6 contains a single crossing line 7 at one focal distance from the lens when the apparatus is set to zero, that is, is set to optical infinity. This line and crossing line are incorporated on a length of film 5 or other similar material that is movable by the person using the device, in a direction parallel to the persons line-of-sight. If the device is constructed so that the crossing line has a range of movement of plus or minus 2.5 centimeters relative to the zero (infinity) setting, this corresponds to settings of plus or minus 10 diopters. As a person uses an optometer constructed as disclosed herein he sees an "X" image with a crossing line located in some apparent vertical position on the "X". The person's point of accommodation is indicated by the placement of the intersection of the "X". The person may then physically move the position of the crossing line, relative to the position of the intersection of the "X", to that point where the crossing line coincides with the intersection of the "X". In making this adjustment the person will be physically moving the crossing line either closer or farther away from the positive lens in the apparatus. This change in position can be read by a number of means. In the preferred embodiment disclosed herein the position of the crossing line is read by the simultaneous movement of an encoded area on the film containing the line and crossing line across an array of photodetectors and emitters creating a signal. This signal can be sent to any known apparatus to convert the signal to a viewable indicator. The signal can also be sent directly to a computer and there used as desired.

Obviously, many modifications and variations of the present invention are possible in light of the above teachings. It is therefore to be understood that, within the scope of the appended claims, the invention may be practiced otherwise than as specifically described.

What is claimed is:

1. An optometer apparatus for measuring the accommodative state of an eye of a person, the optometer apparatus comprising:
   a pinhole aperture plate with center and a plurality of apertures for viewing by a person's eye;
   a positive lens disposed near the pinhole aperture plate and having an optical axis coincident with the center of the pinhole aperture plate; and
   and a movable extended image source oriented such that various parts of the extended image source are simultaneously at differing focal distances from the positive lens.

2. The optometer apparatus of claim 1 wherein the plurality of apertures includes first and second apertures positioned on opposite sides of the center of the pinhole aperture plate.

3. The optometer apparatus of claim 1 wherein the positive lens is a positive Badal lens.

4. The optometer apparatus of claim 1 wherein the plurality of apertures are Scheiner apertures.

5. The optometer apparatus of claim 1 implemented with a means of converting the relative position of the movable extended image source into a machine-readable format.

6. The optometer apparatus of claim 1 implemented with markings on the extended image source to assist in adjustment of the apparatus.

7. The apparatus of claim 6 wherein the markings on the extended image source are comprised of transparent material and the optometer apparatus further includes a means of back illuminating the extended image source.

8. The optometer apparatus of claim 7 wherein the back illuminating means includes a light source for emitting light to backlight the extended image source and a power source for supplying power to the light source.

9. The optometer apparatus of claim 8 wherein the light source is a monochromatic light source for emitting light at a preselected wavelength.

* * * * *